(12) United States Patent
Flavell et al.

(10) Patent No.: US 10,839,954 B2
(45) Date of Patent: Nov. 17, 2020

(54) DYNAMIC EXERCISE CONTENT

(75) Inventors: Andrew C. Flavell, Medina, WA (US); Daniel G. Kennett, Redmond, WA (US); David C. McCarthy, Mercer Island, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

(21) Appl. No.: 13/528,689

(22) Filed: Jun. 20, 2012

(65) Prior Publication Data

US 2013/0316316 A1 Nov. 28, 2013

(30) Foreign Application Priority Data

May 23, 2012 (CA) ........................................ 2777742

(51) Int. Cl.
*G09B 19/00* (2006.01)
*G16H 20/30* (2018.01)

(52) U.S. Cl.
CPC ... *G16H 20/30* (2018.01); *G06T 2207/30196* (2013.01)

(58) Field of Classification Search
CPC ...................................................... G06F 19/34
USPC ......................................................... 434/247
See application file for complete search history.

(56) References Cited

U.S. PATENT DOCUMENTS

| | | | |
|---|---|---|---|
| 5,249,967 A * | 10/1993 | O'Leary et al. | ............. 434/247 |
| 7,967,728 B2 | 6/2011 | Zavadsky et al. | |
| 8,079,938 B2 | 12/2011 | Jones et al. | |
| 8,165,146 B1 * | 4/2012 | Melick | ................. H04B 1/7163 370/390 |
| 2007/0265138 A1 * | 11/2007 | Ashby | ............................ 482/8 |
| 2008/0096726 A1 | 4/2008 | Riley et al. | |
| 2008/0141135 A1 | 6/2008 | Mason et al. | |
| 2008/0281249 A1 | 11/2008 | Gertner | |
| 2009/0051544 A1 | 2/2009 | Niknejad | |
| 2011/0134251 A1 * | 6/2011 | Kim | ...................... H04N 5/232 348/164 |

(Continued)

FOREIGN PATENT DOCUMENTS

CN 2708957 7/2005
CN 102451544 5/2012

(Continued)

OTHER PUBLICATIONS

"Foreign Office Action", Canadian Application No. 2777742, (dated Nov. 9, 2012), 5 pages.

(Continued)

*Primary Examiner* — James B Hull

(57) ABSTRACT

Techniques for dynamic exercise content are described. In implementations, exercise content is provided that includes a variety of different selectable exercise segments that can be individually selected and played back to generate an exercise routine. For example, particular exercise segments can be selected based on user-specified exercise goals, the physical abilities of a particular user, based on various types of feedback, and so on. To assist in the selection of particular exercise segments, exercise segments can be individually tagged with descriptive information, such as using metadata tags. Embodiments can also provide a variety of different types of performance-related feedback to a user during an exercise routine.

20 Claims, 16 Drawing Sheets

(56) References Cited

U.S. PATENT DOCUMENTS

| | | | |
|---|---|---|---|
| 2011/0201476 | A1 | 8/2011 | Solomon |
| 2011/0251021 | A1 | 10/2011 | Zavadsky et al. |
| 2011/0270135 | A1 | 11/2011 | Dooley et al. |
| 2011/0273552 | A1 | 11/2011 | Wang et al. |
| 2011/0281249 | A1 | 11/2011 | Gammell et al. |
| 2012/0116550 | A1 | 5/2012 | Hoffman et al. |
| 2012/0120218 | A1 | 5/2012 | Flaks et al. |
| 2013/0013583 | A1* | 1/2013 | Yu ................. G06F 17/3084 707/709 |
| 2013/0173531 | A1* | 7/2013 | Rinearson ........ G06F 17/30011 707/608 |

FOREIGN PATENT DOCUMENTS

| | | |
|---|---|---|
| CN | 103413018 | 12/2013 |
| WO | WO-2008008729 | 1/2008 |
| WO | WO-2011045726 | 4/2011 |

OTHER PUBLICATIONS

"Foreign Office Action", Canadian Application No. 2777742, (dated Sep. 7, 2012), 4 pages.

"Foreign Office Action", Canadian Application No. 2777742, (dated Feb. 11, 2013), 4 pages.

"Foreign Office Action", Canadian Application No. 2777742, (dated Jun. 26, 2013), 3 pages.

"Foreign Notice of Allowance", CA Application No. 2,777,742, dated Jun. 20, 2014, 1 Page.

"Foreign Office Action", CA Application No. 2,777,742, dated Mar. 5, 2014, 3 Pages.

"International Search Report and Written Opinion", Application No. PCT/US2013/041037, dated Oct. 22, 2013, 13 Pages.

"Foreign Office Action", CA Application No. 2,777,742, dated Nov. 15, 2013, 4 Pages.

"Foreign Office Action", CN Application No. 201310194245.8, dated Nov. 4, 2015, 13 Pages.

"Foreign Office Action", CN Application No. 201310194245.8, dated Jun. 24, 2016, 7 Pages.

"Foreign Notice of Allowance", CN Application No. 201310194245.8, dated Dec. 27, 2016, 4 pages.

"Office Action Issued in Canadian Patent Application No. 2854001", dated May 28, 2018, 3 Pages.

"Office Action Issued in European Patent Application No. 13728569.8", dated Jan. 23, 2019, 2 Pages.

"Search Report Issued in European Patent Application No. 19174502.5", dated Oct. 8, 2019, 9 Pages.

"Office Action Issued in European Patent Application No. 19174502.5", dated Apr. 24, 2020, 8 Pages.

Matthew, Tang, "Recognizing Hand Gestures with Microsoft's Kinect", Retrieved From https://stacks.stanford.edu/file/druid:my512gb2187/Tang_Hand_Gesture_Recognition.pdf, Jan. 1, 2011, 12 Pages.

\* cited by examiner

DYNAMIC EXERCISE CONTENT

PRIORITY CLAIM

This application claims priority under 35 U.S.C. § 119 to Canadian Patent Application Serial No. 2,777,742 filed in Canada on May 23, 2012 and titled "Dynamic Exercise Content," the disclosure of which is incorporated by reference in its entirety herein.

BACKGROUND

The market for physical fitness products continues to grow. Among these products are fitness videos that present various types of exercises to a user. For example, a typical fitness video presents a series of exercises that a user can exercise along with. While such videos can be helpful in certain scenarios, they typically provide a linear series of exercises that do not account for the goals and abilities of individual users.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Techniques for dynamic exercise content are described. In implementations, exercise content is provided that includes a variety of different selectable exercise segments that can be individually selected and played back to generate an exercise routine. For example, particular exercise segments can be selected based on user-specified exercise goals and/or the physical abilities of a particular user.

Implementations can also enable exercise segments to be selected based on various types of feedback, such as based on a user's performance during an exercise routine. Feedback can also include commands from a user. For example, commands can be provided by a user via voice input, gestures, poses, and so on. Thus, implementations enable exercise segments to be dynamically selected during an exercise routine to provide a customized exercise experience, such as based on user performance, user commands, and so on.

To assist in the selection of particular exercise segments, exercise segments can be individually tagged with descriptive information, such as using metadata tags. When a particular type and/or category of exercise content is to be retrieved, the tags can be searched to locate exercise segments that correspond to the appropriate type and/or category.

Embodiments can also provide a variety of different types of feedback to a user during an exercise routine. For example, performance feedback can be provided that suggests ways of improving the user's form while performing an exercise.

BRIEF DESCRIPTION OF THE DRAWINGS

The detailed description is described with reference to the accompanying figures. In the figures, the left-most digit(s) of a reference number identifies the figure in which the reference number first appears. The use of the same reference numbers in different instances in the description and the figures may indicate similar or identical items.

DETAILED DESCRIPTION

Overview

Figure 1:
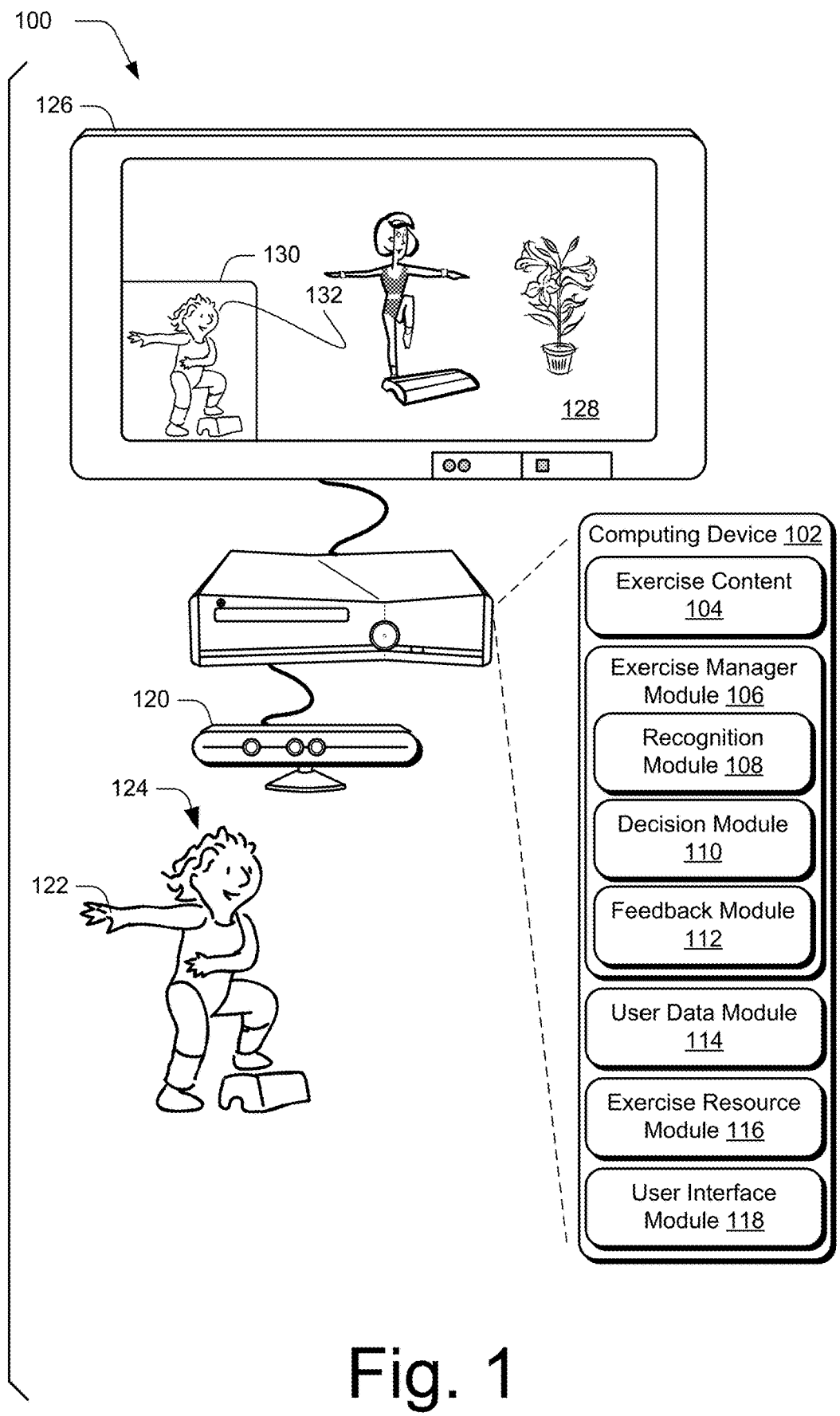
FIG. 1 is an illustration of an environment in an example implementation that is operable to employ techniques discussed herein.

Techniques for dynamic exercise content are described. In implementations, exercise content is provided that includes a variety of different selectable exercise segments. For example, exercise content can include multiple exercise-related content streams that are divided into multiple selectable segments. Particular exercise segments can include a variety of different content types, such as live action video, animation, computer-generated imagery (CGI), audio, and so on. Different exercise segments can also include different types and/or forms of exercise-related activities. For example, some exercise segments can include exercises that focus on muscle building, while others can include cardio-based exercises.

In implementations, exercise segments can be individually selected for playback an exercise routine. For example, particular exercise segments can be selected based on user-specified exercise goals and/or the physical abilities of a particular user. A user, for instance, can indicate the goals of increasing their cardiovascular ("cardio") fitness, as well as the strength of their core muscles. Using on this information, exercise segments of exercise content can be selected that correspond to cardio fitness and core muscle strength. The exercise segments can be played back for the user, such that the user can exercise along with the exercise segments.

Implementations can also enable exercise segments to be selected based on various types of feedback. For example, a natural user interface (NUI) device can be utilized to detect a user's performance during an exercise routine. A user's performance can be based on physical poses, movements, gestures, and so on, that are detected from a user during an exercise routine. Aspects of the user's performance can be recognized and interpreted to customize various aspects of an exercise routine. For example, based on a tempo with which a user is performing an exercise, techniques can detect that the user appears to be getting tired. Thus, a less strenuous exercise segment can be retrieved and played to enable the user to recover.

Feedback can also include commands from a user. For example, commands can be provided by a user via voice input, gestures, poses, and so on. Commands can be detected (e.g., by an NUI device) and recognized to cause various actions to occur. A user, for instance, can say "restart this set." In response, a particular exercise segment or portion of an exercise segment can be restarted. As another example, a user can say "I'm tired." In response, a less strenuous exercise segment (e.g., a rest segment) can be retrieved and played back. Thus, implementations enable exercise segments to be dynamically selected during an exercise routine to provide a customized exercise experience, such as based on user performance, user commands, and so on.

To assist in the selection of particular exercise segments, exercise segments can be individually tagged with descriptive information, such as using metadata tags. When a particular type and/or category of exercise content is to be retrieved, the tags can be searched to locate exercise segments that correspond to the appropriate type and/or category.

Embodiments can also provide a variety of different types of feedback to a user during an exercise routine. For example, an NUI device can detect that a user is not performing a particular exercise using proper form. To assist the user in achieving proper form, performance feedback can be provided that suggests ways of improving the user's form. For example, audible feedback can suggest ways of improving form, such as "try to straighten your back." As another example, visual feedback can visually demonstrate proper form for an exercise, such as by displaying an animated character that is performing the exercise using proper form. A variety of other types of performance feedback can be implemented, and are discussed below.

Techniques can augment visual aspects of exercise content to enhance an exercise experience. For example, using image processing techniques, actors and/or props can be visually altered or removed from exercise content. Further, video images of users and/or objects captured during an exercise routine can be inserted into a scene during playback of exercise content, e.g., in real time. Thus, implementations enable exercise content to be visually altered during playback to provide a customized exercise experience.

In the following discussion, an example environment is first described that is operable to employ techniques for dynamic exercise content described herein. Next, a section entitled "Exercise Content" describes example implementations of exercise content in accordance with one or more embodiments. Following this, a section entitled "Exercise Content Tagging" describes example implementations for tagging exercise content with descriptive information in accordance with one or more embodiments. Next, a section entitled "Content Creation Environment" describes an example environment that may be employed to create exercise content in accordance with one or more embodiments.

Following this, a section entitled "Generating Exercise Routines" describes example implementations for generating different exercise routines in accordance with one or more embodiments. Next, a section entitled "Dynamic Modification of Exercise Routines" describes example implementations for dynamically modifying exercise routines in accordance with one or more embodiments. Following this, a section entitled "Augmentation of Exercise Content" describes example implementations for augmenting exercise content in accordance with one or more embodiments. Finally, an example system and device are described that are operable to employ techniques discussed herein in accordance with one or more embodiments.

Example Environment

FIG. 1 is an illustration of an environment 100 in an example implementation that is operable to implement techniques for dynamic exercise content discussed herein. The illustrated environment 100 includes a computing device 102. Although the computing device 102 is illustrated as a game console, the computing device 102 may be configured in a variety of other ways. For instance, the computing device 102 may be configured as a desktop computer, a mobile station, an entertainment appliance, a set-top box communicatively coupled to a display device, a mobile communication device (e.g., a tablet, a smartphone), and so forth.

Accordingly, the computing device 102 may range from full resource devices with substantial memory and processor resources (e.g., personal computers, game consoles) to low-resource devices with limited memory and/or processing resources (e.g., traditional set-top boxes, hand-held game consoles). Additionally, although a single computing device 102 is shown, the computing device 102 may be representative of a plurality of different devices, such as a user-wearable helmet and game console, multiple servers utilized by a business to perform operations that provide a cloud-based platform, a remote control and set-top box combination, and so on. One of a variety of different examples of a computing device 102 is shown and described below in FIG. 16.

Included as part of the computing device 102 is exercise content 104, which is representative of various types of exercise-related content that can be consumed by a user. In implementations, the exercise content 104 can be stored locally on the computing device 102, and/or can be stored on some form of removable computer-readable storage media. For example, the exercise content 104 can be stored on a digital versatile disc (DVD) that can be read by the computing device 102. Alternatively or additionally, the exercise content 104 can be stored on a network resource, such as a cloud resource discussed below with reference to FIG. 16. For example, the exercise content 104 can be embodied as cloud-based content that can be streamed to the computing device 102 from a remote resource. A detailed example of the exercise content 104 is discussed below.

The computing device 102 further includes an exercise manager module 106, which is representative of functionality for performing various tasks related to the techniques for dynamic exercise content discussed herein. The exercise manager module 106 includes a recognition module 108, which is representative of functionality to receive and recognize various forms of input for the exercise manager module 106. For example, the recognition module 108 can be configured to receive input generated by an input device, such as a keyboard, a mouse, a touchpad, a game controller, an optical scanner, and so on. The recognition module 108 can also be configured to receive and/or interpret input received via a touchless mechanism, such as via voice recognition, gesture-based input, detected body poses and body motions, object scanning, and so on.

The exercise manager module 106 further includes a decision module 110, which is representative of functionality to make various decisions concerning the selection and playback of exercise content. For example, based on user performance recognized by the recognition module 108, the decision module 110 can determine specific types of exercise content (e.g., exercise segments) that are to be retrieved for playback. The decision module 110 can also receive user commands, and can alter and/or select exercise content based on the user commands.

Also included is a feedback module 112, which is representative of functionality to provide feedback regarding various aspects of user performance. For example, functionalities of the exercise manager module 106 can determine that a user is displaying improper form while attempting to perform an exercise, such as an exercise that currently being played back from the exercise content 104. To assist the user in improving their form, the feedback module 112 can provide feedback that includes example ways of improving the user's form. Such feedback can include audible feedback, video feedback, and so on.

Further included is a user data module 114, which is representative of functionality to store various user-specific information. For example, the user data module 114 stores identifiers that are each specific to an individual user such that users can be differentiated from one another. The user data module 114 further associates user exercise data for individual users with the users' identifiers so that user exercise data can be retrieved for respective users. Examples of user exercise data include user profiles (e.g., age, gender, weight, and so on), user preferences, user exercise history, and so forth. Techniques discussed herein can utilize the user exercise data to generate custom exercise experiences for individual users. For example, techniques can retrieve portions of exercise content that correspond to user exercise data. Further, techniques can update user exercise data based on detected user performance during an exercise routine. As discussed below, updating user exercise data enables user exercise experiences for individual users to evolve as more information about the users is received.

The computing device 102 further includes exercise resource module 116 and a user interface module 118. The exercise resource module 116 is representative of functionality to store different types of exercise-related information that can be accessed by various entities, such as the exercise manager module 106. An example implementation of the exercise resource module 116 is presented below. The user interface module 118 is representative of functionality to manage various user interface aspects for the exercise content 104 and/or the exercise manager module 106. Examples of such user interfaces include audible user interfaces, graphical user interfaces (GUIs), tactile user interfaces (e.g., for touch input), and so on.

Further included as part of the computing device 102 is an NUI device 120, which is configured to receive a variety of touchless input, such as via visual recognition of human gestures, object scanning, voice recognition, color recognition, and so on. In at least some embodiments, the NUI device 120 is configured to recognize gestures, poses, body movements, objects, images, and so on, via cameras. An example camera, for instance, can be configured with lenses, light sources, and/or light sensors such that a variety of different phenomena can be observed and captured as input. For example, the camera can be configured to sense movement in a variety of dimensions, such as vertical movement, horizontal movement, and forward and backward movement, e.g., relative to the NUI device 120. Thus, in at least some embodiments, the NUI device 120 can capture information about image composition, movement, and/or position. The recognition module 108 can utilize this information to perform a variety of different tasks.

For example, the recognition module 108 can leverage the NUI device 120 to perform skeletal mapping along with feature extraction with respect to particular points of a human body (e.g., different skeletal points) to track one or more users (e.g., four users simultaneously) to perform motion analysis. In at least some embodiments, feature extraction refers to the representation of the human body as a set of features that can be tracked to generate input. For example, the skeletal mapping can identify points on a human body that correspond to a right hand 122 of a user 124. The recognition module 108 can use feature extraction techniques to recognize the points as a right hand and to characterize the points as a feature that can be tracked and used to generate input. Further to at least some embodiments, the NUI device 120 can capture images that can be analyzed by the recognition module 108 to recognize one or more motions and/or positioning of body parts or other objects made by a user, such as what body part is used to make a motion, a position (e.g., angle) of a body part relative to other body parts, which user made a motion, and so on.

In implementations, a variety of different types of gestures may be recognized, such as gestures that are recognized from a single type of input as well as gestures combined with other types of input, e.g., a hand gesture and voice input. Thus, the recognition module 108 can support a variety of different gestures and/or gesturing techniques by recognizing and leveraging a division between inputs. It should be noted that by differentiating between inputs of the NUI device 120, a particular gesture can be interpreted in a variety of different ways when combined with another type of input. For example, although a gesture may be the same, different parameters and/or commands may be indicated when the gesture is combined with different types of inputs. Additionally or alternatively, a sequence in which gestures are received by the NUI device 120 can cause a particular gesture to be interpreted as a different parameter and/or command. For example, a gesture followed in a sequence by other gestures can be interpreted differently than the gesture alone.

The computing device 102 further includes a display device 126, which displays an exercise GUI 128 generated and managed according to various techniques discussed herein. For example, the GUI 128 displays various portions of the exercise content 104, such as exercise segments selected from the exercise content 104 utilizing techniques discussed herein.

The GUI 128 includes a user region 130, which displays a user representation 132 of the user 124. For example, the user region 130 can be a picture-in-picture (PIP) display that overlays a portion of the GUI 128. The user representation 132 is a likeliness of the user 124 that can be generated in a variety of ways. For example, the user representation 132 can be a real-time video image of the user 124, e.g., as captured by a video camera such as utilized by the NUI device 120. The user representation 132 can also be an animated version of the user 124, such as an avatar that is generated using computer animation and/or CGI techniques. Still further, the user representation 132 can be generated by enhancing a live video image of the user 124 using 2-dimensional (2D) and/or 3-dimensional (3D) computer graphics techniques. Thus, in implementations the user representation 132 can move along with the user 124 such that movements of the user 124 are reflected in similar movements of the user representation 132, e.g., in real time. Further examples of GUI-related aspects are discussed below.

Having discussed an example environment in which techniques discussed herein can be implemented in accordance with one or more embodiments, consider now a discussion of some example exercise content.

Exercise Content

Figure 2:
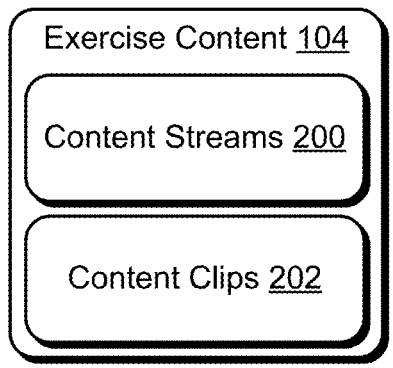
FIG. 2 illustrates an example implementation of exercise content in accordance with one or more embodiments.

FIG. 2 illustrates an example implementation of the exercise content 104, introduced above with reference to FIG. 1. The exercise content 104 includes content streams 200 and content clips 202. The content streams 200 are representative of different streams of exercise content that can be selected for playback. For example, the content streams 200 can include extended portions of linear exercise content, such as entire exercise routines that involve multiple exercises performed in sequence over a particular period of time. Individual of the content streams 200, for instance, can focus on a particular fitness trainer that presents an exercise routine of a particular duration, such as 30 minutes, 60 minutes, 90 minutes, and so on. As discussed above and below, the content streams 200 can be divided into segments that can be individually selected for playback.

The content clips 202 are representative of discrete portions of exercise content that can be selected to form a portion of an exercise routine. For example, the content clips 202 can include short portions of exercise content (e.g., 3 minutes, 5 minutes, 10 minutes, and so on) that focus on one particular exercise and/or group of exercises. Thus, techniques discussed herein can generate workout routines by selecting exercise content from the content streams 200 and/or the content clips 202.

Figure 3:
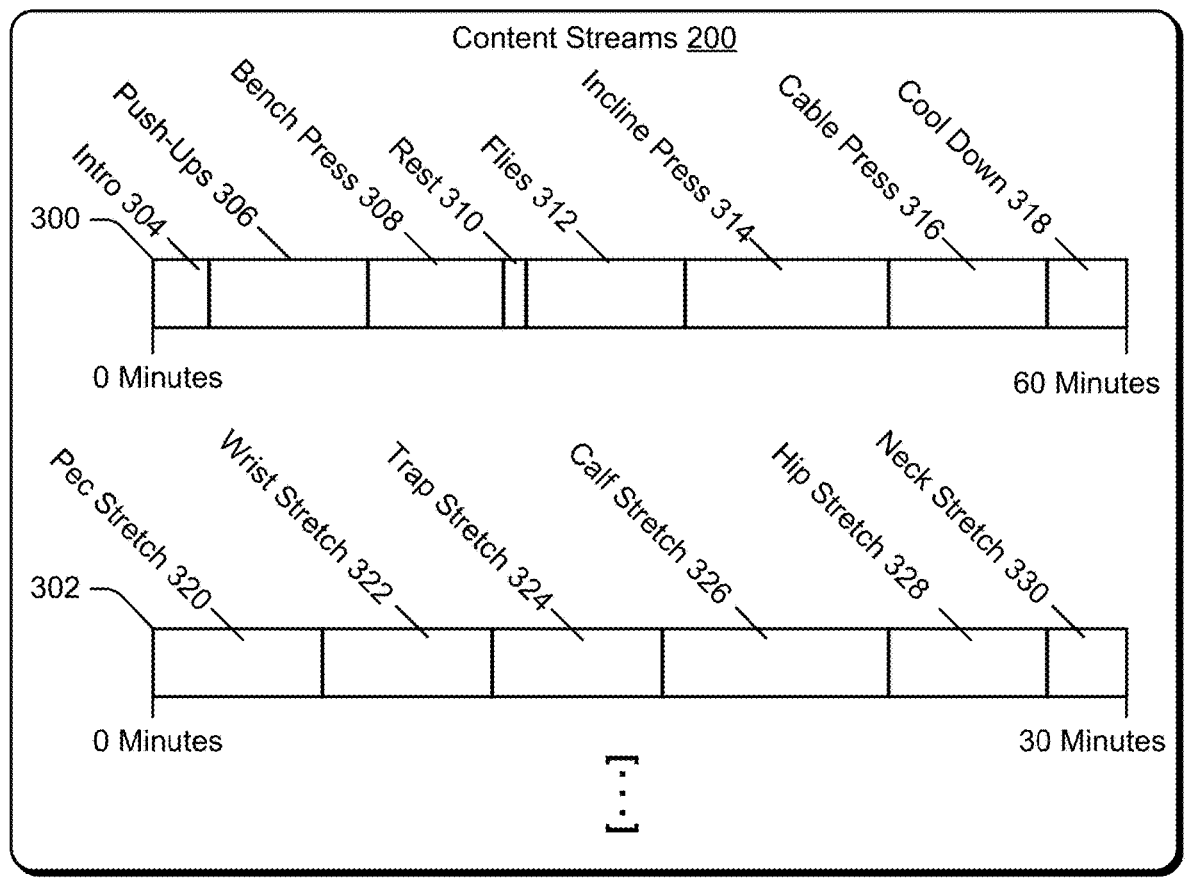
FIG. 3 illustrates an example implementation of content streams in accordance with one or more embodiments.

FIG. 3 illustrates an example implementation of the content streams 200. Included as part of the content streams 200 are a content stream 300 and a content stream 302, which corresponds to linear portions of exercise content.

The content stream 300 is divided into several discrete segments that each corresponds to a subsection of exercise content included as part of the content stream 300. For example, an intro segment 304 corresponds to an introductory segment, and can include information about exercise content included in the content stream 300. The intro segment 304, for instance, can include video content of a trainer explaining various aspects of exercises included as part of the content stream 300.

The content stream 300 further includes a push-up segment 306 and a bench press segment 308, which each correspond to discrete segments of the content stream 300 associated with a particular exercise. For example, the push-up segment 306 can include 10 minutes of push-up exercise content that can be selected for playback. Further included is a rest segment 310, which includes content that corresponds to a rest period in the content stream 300. For example, the rest segment 310 can include video content of a trainer providing instruction to take a 1 minute rest and drink some water.

Further included as part of the content stream are a flies segment 312, an incline press segment 314, and a cable press segment 316. Each of these segments corresponds to a particular segment of exercise content. The content stream 300 further includes a cool down segment 318, which includes content that can provide instruction for cooling down after an exercise routine.

The content stream 302 is also divided into a number of discrete segments of exercise content. For example, the content stream 302 includes a pectoral stretch segment 320, a wrist stretch segment 322, a trap stretch segment 324, a calf stretch segment 326, a hip stretch segment 328, and a neck stretch segment 330. Thus, the segments included as part of the content stream 302 include stretching-related exercises that can be selected as part of an exercise routine. Accordingly, the segments included as part of the content streams 300, 302 each include a particular type of exercise content, and have a particular time duration. The content streams presented above are illustrated for purposes of example only, and a wide variety of different exercise types and combinations of exercises may be implemented in accordance with the claimed embodiments.

Figure 4:
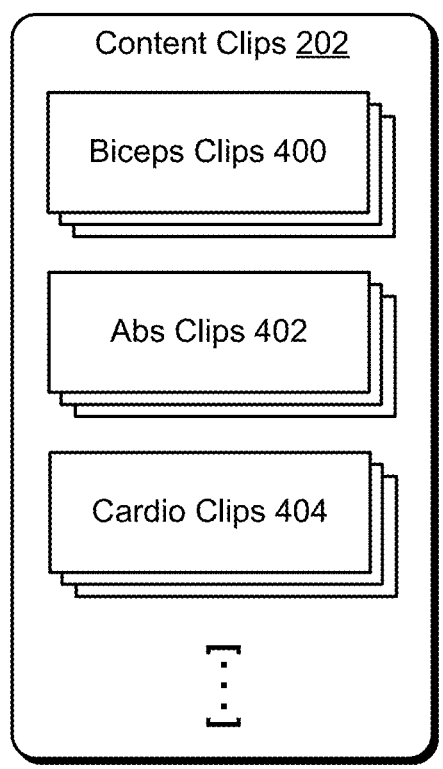
FIG. 4 illustrates an example implementation of content clips in accordance with one or more embodiments.

FIG. 4 illustrates an example implementation of the content clips 202, in accordance with one or more embodiments. As mentioned above, the content clips 202 include discrete portions of exercise content that can be selected to form a portion of an exercise routine. For example, the content clips 202 can be relatively short as compared to the content streams 200, e.g., less than 15 minutes.

The content clips 202 include biceps clips 400, which correspond to different portions of exercise content related to biceps exercises. For example, at least some of the biceps clips 400 can correspond to portions of exercise content associated with different exercise programs, different trainers, and so on. Thus, if a user specifies a preference for a particular trainer, exercises from the biceps clips 400 from that trainer can be selected.

Further included are abs clips 402 and cardio clips 404, which correspond to exercise content related to abdominal muscles and cardiovascular development, respectively. These content clips are provided for purposes of illustration only, and a wide variety of other exercise content may be represented via the content clips 202 in accordance with various embodiments.

Figure 5:
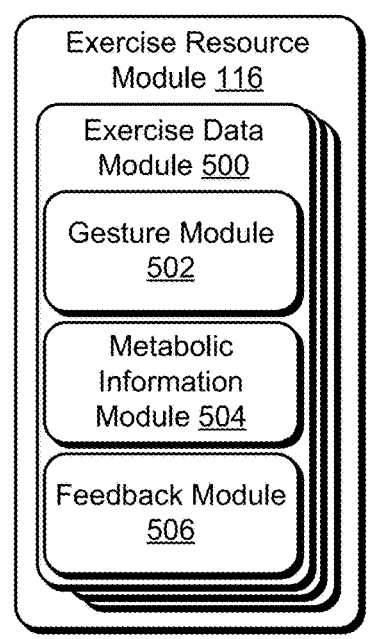
FIG. 5 illustrates an example implementation of an exercise resource module in accordance with one or more embodiments.

FIG. 5 illustrates an example implementation of the exercise resource module 116, in accordance with one or more embodiments. The exercise resource module 116 includes a variety of different information about different exercises that can be implemented as part of an exercise routine.

Included as part of the exercise resource module 116 is an exercise data module 500, which includes information about specific exercises. In implementations, each of multiple different exercise types can have an associated exercise data module 500. For example, the exercise resource module 116 can include different exercise data modules for push-ups, sit-ups, abdominal crunches, and so on. Thus, in implementations each exercise data module can store and/or track information about a specific exercise type.

The exercise data module 500 includes a gesture module 502, a metabolic information module 504, and a feedback module 506. The gesture module 502 includes gesture information for specific exercises. For example, the gesture module 502 can store information for body gestures, motions, and/or poses associated with particular exercises. The metabolic information module 504 includes metabolic information for specific exercises. Metabolic information can include metabolic equivalent of task (MET) values for different exercises. For example, the metabolic information can include MET values for particular exercises based on gender, age, height, weight, and so on.

The feedback module 506 includes feedback information for specific exercises. Feedback information can include feedback that can be provided to a user to assist the user in improving their exercise experience, to motivate and encourage a user during an exercise routine, and so on. For example, the feedback module 506 can include text that can be output as audio to a user to provide various types of exercise-related feedback. The feedback module 506 can also include indications of particular body parts and/or body regions that can be highlighted to provide feedback for particular exercises.

The feedback module 506 may further include video clips that may be played back to provide instruction and/or encouragement to a user. For example, video clips can be played back in the user region 130 and/or inserted into exercise content during playback. A video clip of a trainer, for instance, can pop up during playback of exercise content to provide feedback.

Thus, different exercise data modules 500 can be accessed (e.g., by the exercise manager module 106) to obtain information about specific exercises, such as for deciding which exercises to present to a user, and feedback to provide to a user based on observed user performance.

Exercise Content Tagging

In implementations, exercise content can be tagged with various descriptive information to enable particular types of exercise content to be retrieved. For example, specific segments of exercise content can each include a respective tag (e.g., a metadata tag) that specifies information about its particular segment.

Figure 6:
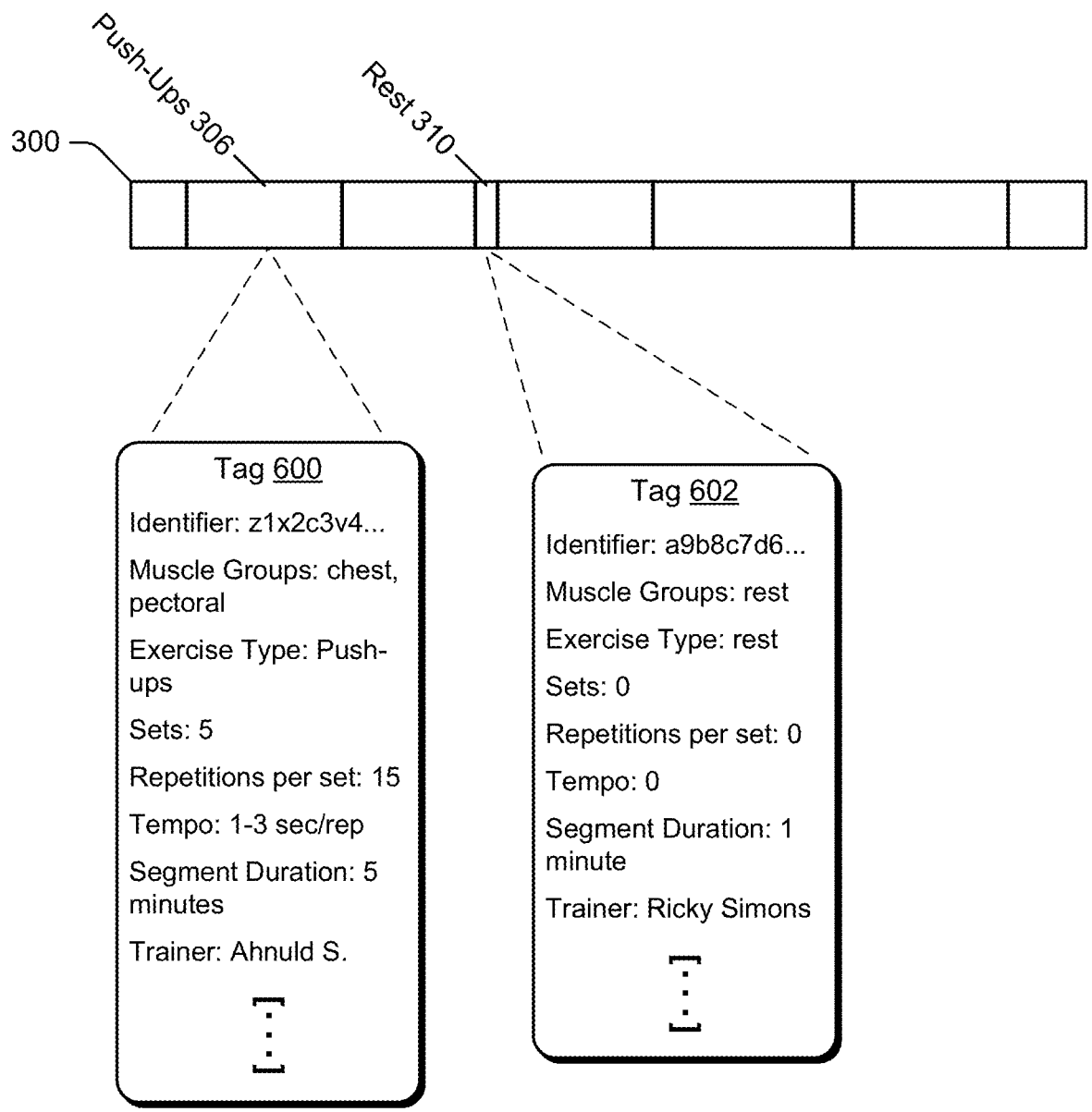
FIG. 6 illustrates an example implementation of content tagging in accordance with one or more embodiments.

FIG. 6 illustrates an example implementation of content tagging in accordance with one or more embodiments. The content stream 300 is illustrated with its respective segments, discussed above. The push-ups segment 306 includes a tag 600, which describes various exercise-related aspects of the push-ups segment 306. For example, the tag 600 includes an identifier for the push-ups segment 306. In implementations, the identifier can be used to distinguish the push-ups segment 306 from other segments and/or portions of exercise content. Thus, implementations can enable the push-ups segment 306 to be located and retrieved via the identifier.

The tag 600 includes other information about the push-ups segment 306, such as muscle groups and exercise types associated with the push-ups segment 306. The tag 600 further identifies a number of sets of exercises, and a number of exercise repetitions per set for the push-ups segment 306. Further, an exercise tempo is specified that indicates an optimum time per repetition.

The tag 600 further specifies a segment duration that indicates a time duration for the push-ups segment 306. Also included is a trainer identifier that specifies trainers and/or actors associated with the push-ups segment 306.

Although not expressly illustrated, the tag 600 can include a variety of other types of information. For example, the tag 600 can include timestamps that indicate the beginning, ending, and/or other portions of exercise reps for the push-ups segment 306. The timestamps can be used to determine whether a user is synchronized with the push-ups segment 306 during playback of the segment. Alternatively or additionally, the tag 600 can include frame stamps that correlate particular video frames with particular portions of exercise reps. The tag 600 can also include metabolic information, such as MET values for particular exercises associated with the tag. Various other types of information are contemplated as well.

The rest segment 310 is also illustrated, which includes a tag 602. The tag 602 indicates various types of information associated with the rest segment 310, and can include a variety of other types of information not expressly listed.

Thus, implementations can associate tags (e.g., as metadata) with segments of exercise content such that descriptive information about exercise content in the segments can be specified via the tags. Exercise clips, such as the content clips 202, can also include tags. The tags can enable multiple segments of different exercise content (e.g., from different content streams) to be searched to identify segments that meet specific search criteria.

Content Creation Environment

Figure 7:
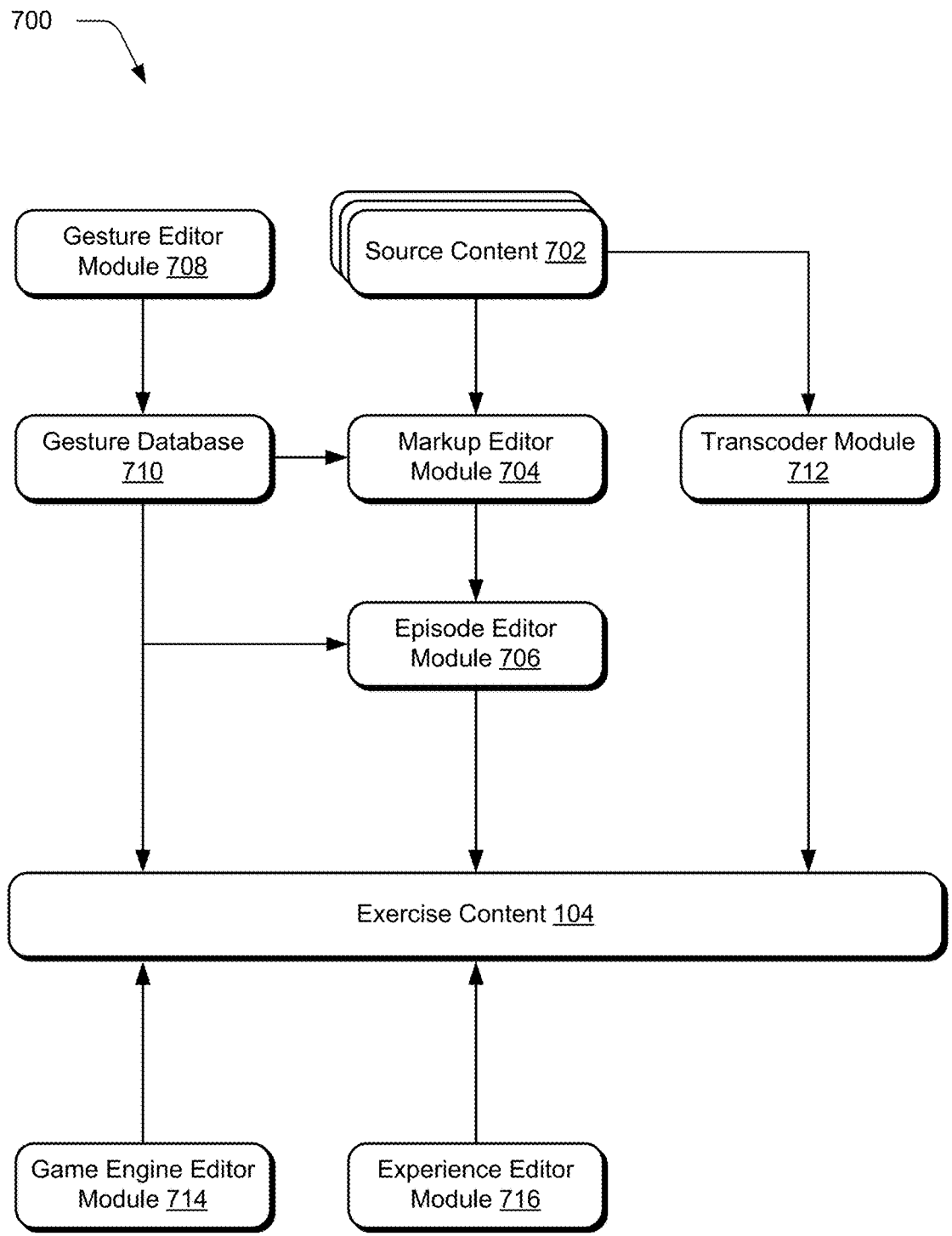
FIG. 7 is an illustration of a creation environment in an example implementation that is operable to employ techniques discussed herein.

FIG. 7 is an illustration of a creation environment 700 in an example implementation that is operable to implement techniques for creating dynamic exercise content. The creation environment 700 includes source content 702, which is representative of various types of content which can be used to create the exercise content 104. For example, the source content 702 can include pre-recorded exercise content, such as a content stream, a content segment, and/or a content clip. In implementations, the exercise content can be "off the shelf" exercise content, such as exercise content that is retrieved from a pre-recorded DVD or other data storage medium, downloaded from a network resource, and so on.

Further illustrated is a markup editor module 704, which is representative of functionality to edit computer code (e.g., hypertext markup language (HTML), extensible markup language (XML), and so forth) of the source content 702. For example, the markup editor module 704 can be employed to apply tags to content segments, clips, and so forth, of the source content 702.

An episode editor module 706 is also included, which is representative of functionality to enable different exercise experiences to be generated via the source content 702. For example, the episode editor module 706 can be leveraged to insert event triggers into portions of content that can be utilized to trigger various events during playback of the exercise content 104. The episode editor module 706 may also be employed to specify various layout parameters for the exercise content 104, and to provide scripting for different exercise experiences that can be played via the exercise content 104.

Further included as part of the creation environment 700 are a gesture editor module 708, and a gesture database 710. The gesture editor module 708 is representative of functionality to associate various gestures with exercise-related movements included as part of the source content 702. For example, gestures can be correlated to physical movements of actors in the source content 702, such as movements that are observed during a particular exercise.

Gestures may also be correlated to particular times (e.g., via timestamps) and/or frames of the source content 702 for purposes of determining whether a user is providing an appropriate gesture during the playback of the exercise content 104. Various gesture editing via the gesture editor module 708 can be stored as part of the gesture database 710. In at least some implementations, the gesture database 710 can be included as part of the exercise resource module 116, discussed above and below.

A transcoder module 712 is provided, which is representative of functionality to convert the source content 702 between different types of data encoding. For example, at least some of the source content 702 in its original form may be encoded using different encoding formats. Thus, the transcoder module 712 can be leveraged to convert the source content 702 into a common encoding format for the exercise content 104.

The creation environment 700 further includes a game engine editor module 714, and an experience editor module 716. The game engine editor module 714 is representative of functionality to enable modifications to a game engine based on particular parameters for the exercise content 104. For example, an existing game engine can be customized using the game engine editor module 714 to provide a tailored game experience for the exercise content 104.

The experience editor module 716 is representative of functionality to provide further customizations to the exercise content 104. For example, the experience editor module 716 can be leveraged to add and/or customize various types of content, such as audio, video (e.g., 2D and/or 3D video editing), graphical user interfaces, and so forth. The experience editor module 716 may also be leveraged to provide localization parameters for the exercise content 104, to enable the exercise content 104 to be customized for different countries, geographic regions, demographics, markets, and so on. In at least some implementations, the experience editor module 716 can provide a pipeline for a variety of different entities and functionalities to customize various aspects of the exercise content 104.

The creation environment 700 is provided for purposes of example only, and the exercise content 104 can be generated and customized via a variety of different functionalities and environments within the spirit and scope of the claimed embodiments. Further, various modules and functionalities of the creation environment 700 may be implemented via different configurations of devices and resources, such as discussed below with reference to FIG. 16.

Generating Exercise Routines

Techniques discussed herein can utilize exercise content to generate exercise routines based on a variety of different factors.

Figure 8:
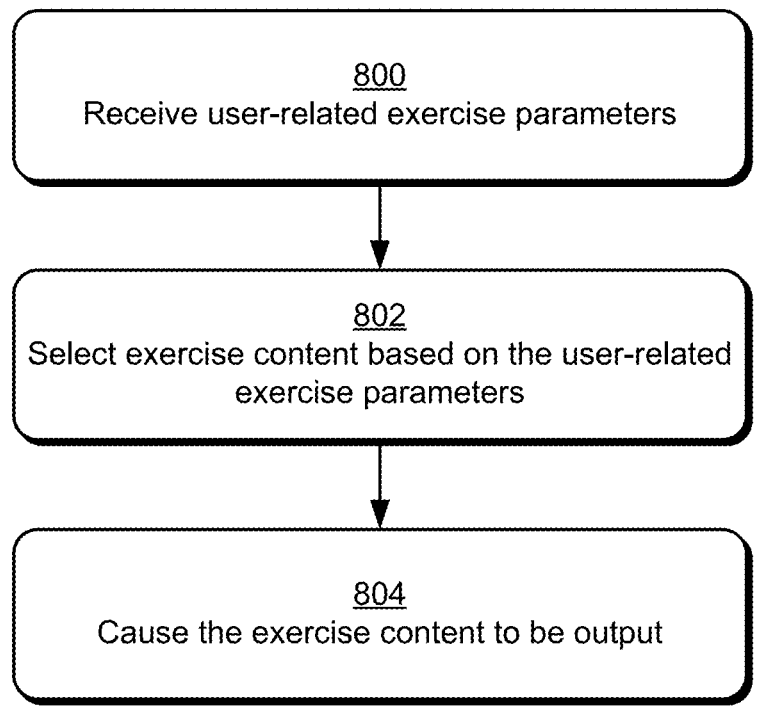
FIG. 8 is a flow diagram that describes steps in a method in accordance with one or more embodiments.

FIG. 8 is a flow diagram that describes steps in a method in accordance with one or more embodiments. Step 800 receives user-related exercise parameters. For example, a user can provide various user-specific information that can be used to generate an exercise routine. User-specific information can include physical attributes of a user, such as gender, age, height, weight, and so on. User specific information can also include exercise-related abilities of the user, such as an indication of a user's exercise experience level. User specific information can further include a user's exercise goals, such as increasing their cardio fitness, losing weight, increasing muscle mass, increasing flexibility, and so on. A user can also specify a particular workout duration, such as 30 minutes, an hour, and so on. A user can provide user-specific information via a variety of different types of input, such as touch input, voice input, gesture input, and so on.

User-related parameters can further include aspects of a user's exercise history. For example, a user's exercise history can be tracked (e.g., by the exercise manager module 106) and stored as part of the user data module 114. The user's exercise history can include which exercises the user has performed during previous exercise sessions, how frequently the user has performed particular exercises during previous exercise sessions, and so on. A user's exercise history can also include the user's performance history and/or progress. For example, if a user's form has improved sufficiently on a particular exercise, the user can be presented with more advanced exercise content. Conversely, if a user's form appears to be getting worse, simpler exercise content and/or exercise content that focuses on particular movements and/or muscle groups can be retrieved to assist the user in improving their form.

User-related parameters can also include detected parameters, such as attributes of a user detected via the NUI device 120 and recognized via the recognition module 108. For example, the exercise manager module 106 can output instructions to a user to perform various tasks, such as jumping jacks, push-ups, and so on. The exercise manager module 106 can compare the user's performance to known parameters for such tasks, such as proper exercise form, average exercise tempo, and so on. From this information, the decision module 110 can ascertain aspects of the user's experience level and/or physical condition.

Step 802 selects exercise content based on the user-related exercise parameters. The decision module 110, for instance, can select segments from the content streams 200 and/or clips from the content clips 202, based on the exercise parameters. For example, aspects of the exercise parameters can be correlated to tags included as part of the exercise content to enable appropriate exercise content to be located and retrieved.

Step 804 causes the exercise content to be output. For example, the exercise content can be streamed for consumption by a user as the exercise content is selected by the decision module 110. Alternatively or additionally, the exercise content can be stored for later consumption by a user.

In implementations, exercise content for an exercise routine can be selected and output in a piecemeal manner, instead of preselecting exercise content for an entire exercise routine prior to beginning playback. For example, for a 60 minute exercise routine, a first set of exercise segments for the first 10 minutes of the routine can be selected. Playback of the first set of segments can then begin. During the playback, various feedback can be detected, such as user-associated feedback, environment feedback, social network feedback, and so on. Based on the feedback, subsequent exercise segments can be retrieved and output, e.g., after playback of the first set of segments is complete. This process can continue until the exercise routine is complete, thus enabling the exercise routine to dynamically change and adapt based on various types of feedback and information.

Figure 9:
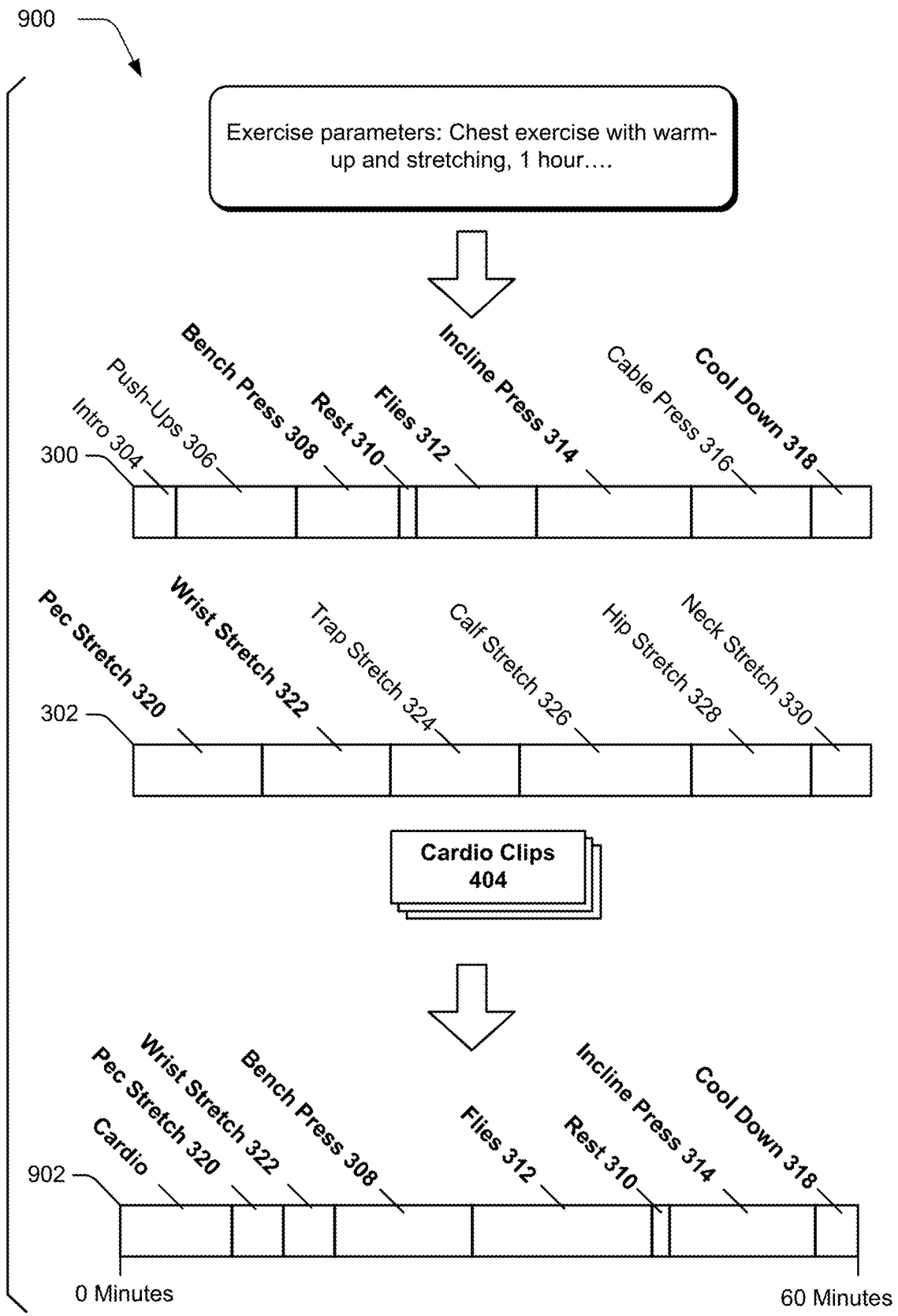
FIG. 9 illustrates an example implementation scenario in accordance with one or more embodiments.

FIG. 9 illustrates an example implementation scenario in which portions of exercise content are selected for playback, generally at 900. In the upper portion of the scenario 900, various exercise parameters are received to be used to select exercise content. For example, the exercise parameters indicate a one hour exercise routine that focuses on chest exercises and includes a warm-up and stretching.

Continuing to the center portion of the scenario 900, segments from the content streams 300, 302 are selected. Further, a clip from the cardio clips 404 is selected, e.g., for a warm-up portion of an exercise routine. For example, the segments and clip can be selected by the decision module 110.

Proceeding to the lower portion of the scenario 900, the selected portions are assembled into an exercise routine 902. The exercise routine 902 can be played back such that a user can exercise along with the exercise routine 802.

Dynamic Modification of Exercise Routines

Techniques discussed herein can dynamically modify exercise routines based on a variety of different factors. For example, an exercise routine can be dynamically modified "on the fly" during playback of the exercise routine.

Figure 10:
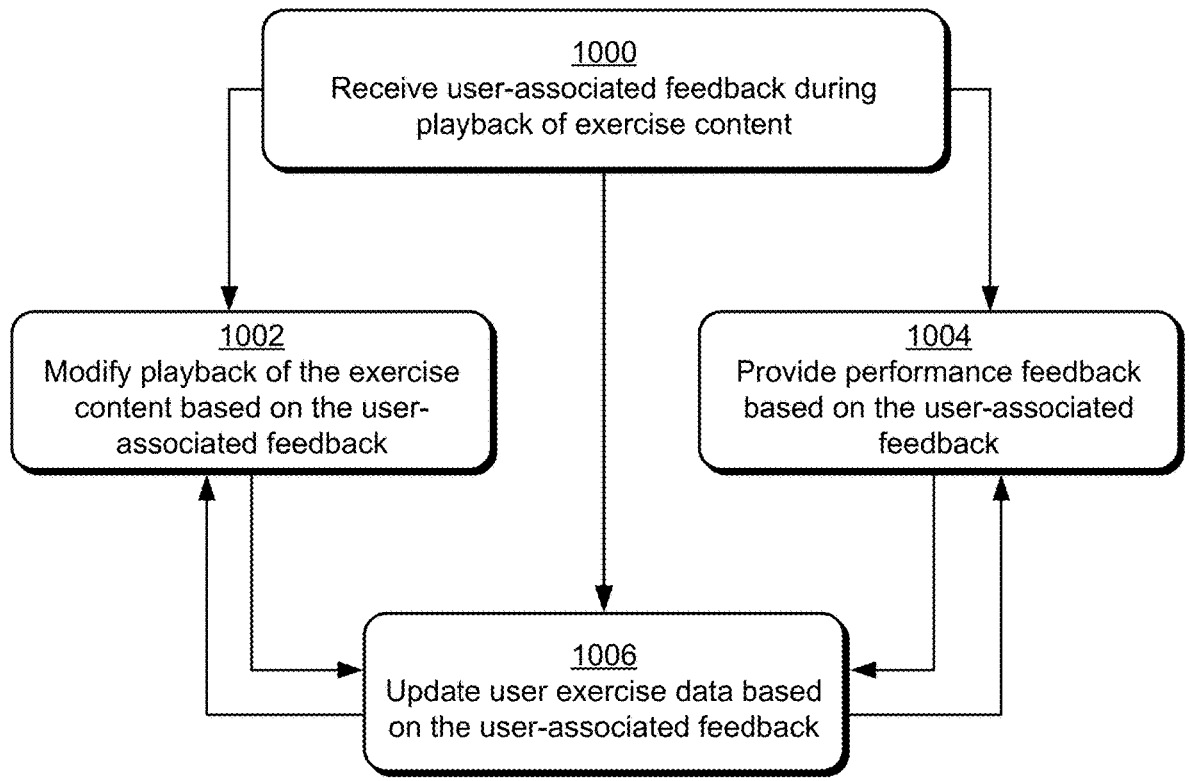
FIG. 10 is a flow diagram that describes steps in a method in accordance with one or more embodiments.

FIG. 10 is a flow diagram that describes steps in a method in accordance with one or more embodiments. Step 1000 receives user-associated feedback during playback of exercise content. For example, the NUI device 120 can detect user gestures, motion, poses, and so on, which the recognition module 108 can recognize as indicating certain various aspects of user performance. The user performance, for instance, can indicate that the user is having difficulty performing a particular exercise with proper form. Thus, user-associated feedback can include "passive feedback" that is based on detected aspects of user performance.

User-associated feedback can also include "active feedback" that is provided by a user. Active feedback can include explicit voice and/or gesture-based feedback from a user, such as a user saying "my lower back hurts" or "I need a drink of water." Also, specific gestures can be defined that have particular meanings, such as a gesture that indicates "I'm tired" or "repeat that segment."

Another form of user-associated feedback can include biological feedback obtained via a variety of different sensors, such as a heart rate monitor, a respiration rate monitor, and so on. For example, a low heart rate observed during cardio exercise can indicate that the user is not exercising within the user's cardio heart rate zone. Conversely, a heart rate that is too high can indicate that a user is over-exerting themselves. These forms of user-associated feedback are just a few examples, and a variety of types of feedback and sensors can be utilized in accordance with the claimed embodiments.

Step 1002 modifies playback of the exercise content based on the user-associated feedback. For example, the modification can include retrieving different segments and/or clips of exercise content, repeating exercise content that has already been played, rearranging exercise content that has already been retrieved, and so on. Further, the modification can occur on-the-fly, e.g., during playback of the exercise content.

For instance, consider a scenario where the user-associated feedback indicates that a user is having trouble keeping up with the tempo of a particular exercise segment. In response, a different segment can be retrieved that includes a similar exercise but with a slower tempo. The different segment can replace the particular exercise segment during playback of the exercise content. As discussed above, segments and clips of exercise content can be retrieved by searching their tags based on information included in the tags.

Step 1004 provides performance feedback based on the user-associated feedback. The feedback module 112, for instance, can locate appropriate performance feedback to be provided to the user based on performance attributes (e.g., passive feedback) indicated by the user-associated feedback. Performance feedback can include text and/or audible feedback, such as "pick up the pace" or "keep your legs straight."

Performance feedback can also include visual feedback, such as visually highlighting a region of the user representation 132 that corresponds to an area of a user's body that is relevant to the performance feedback. For example, consider a scenario where the user representation 132 is displayed during playback of an exercise segment that includes squat thrusts. If the user is not bending their knees enough, the knee region of the user representation 132 can be visually highlighted. Additionally, text and/or audible output can be provided that says "bend your knees a little more."

Color coding can also be implemented as part of visual highlighting to convey particular meanings. For example, green highlighting can indicate that a user's performance is within acceptable parameters for a particular exercise. Yellow highlighting can indicate that the user is trending away from acceptable performance in one or more aspects of an exercise. Red highlighting can indicate that the user is failing to perform one or more aspects of an exercise correctly. With reference to the scenario above, the knee region of the user representation can be colored yellow or red to indicate that the user is not bending their knees enough.

Step 1006 updates user exercise data based on the user-associated feedback. For example, the user data module 114 can link the user-associated feedback with a particular user identifier, and can store the user-associated feedback so that it can be later retrieved to determine appropriate exercise content to present to the user. In implementations, steps 1002, 1004, and 1006 can occur in parallel, in series, alternatively, and/or combinations thereof.

Figure 11:
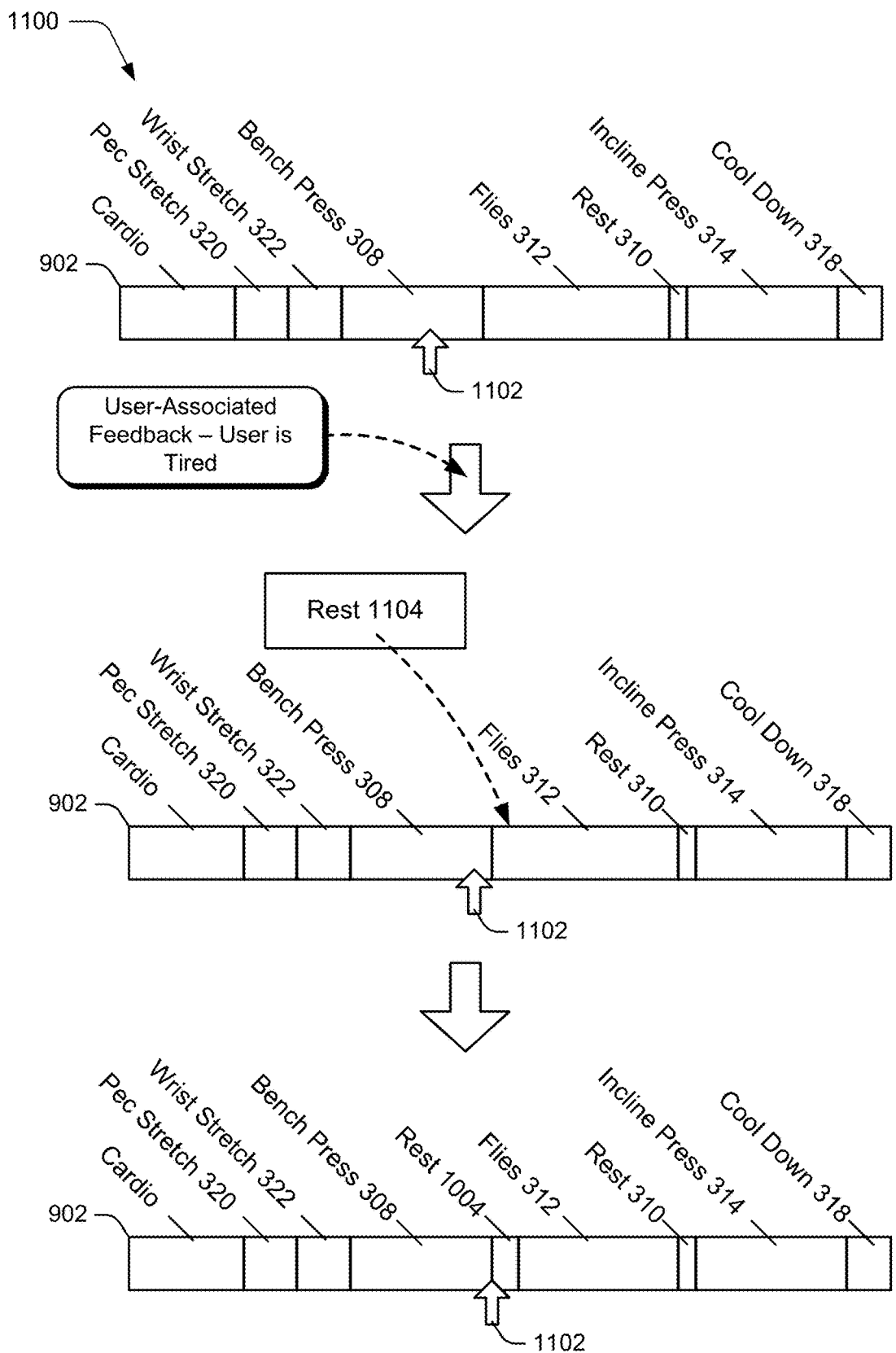
FIG. 11 illustrates an example implementation scenario in accordance with one or more embodiments.

FIG. 11 illustrates an example implementation scenario in which an exercise routine is dynamically modified, generally at 1100. Starting with the upper portion of the scenario 1100, a user exercises along with the playback of the exercise routine 902, discussed above. The playback progress of the exercise routine 902 is indicated by the progress indicator 1102.

Continuing to the middle portion of the scenario 1100, user-associated feedback is received that indicates that the user is tired after finishing the bench press segment 308 of the exercise routine 902. In response to the user-associated feedback, a rest segment 1104 is retrieved. For example, the rest segment 1104 can be retrieved from the content streams 200, the content clips 202, and so on.

Continuing to the lower portion of the scenario 1100, the rest segment 1104 replaces a portion of the flies segment 312. Accordingly, instead of transitioning directly from the bench press segment 308 to the flies segment 312, the rest segment 1104 is inserted between the segments. Thus, the exercise routine 902 is dynamically modified during playback to provide a user with an additional rest period.

Summary sections may also be inserted during playback of exercise content, such as during a rest period. A summary section can indicate user progress at a particular point during an exercise routine, such as performance attributes for particular exercises, calories burned thus far, performance contrasted with previous (e.g., historical) exercise routines, and so on. Optionally, a detailed summary section may be provided at the end of a workout routine, such as during a cool down segment.

Figure 12:
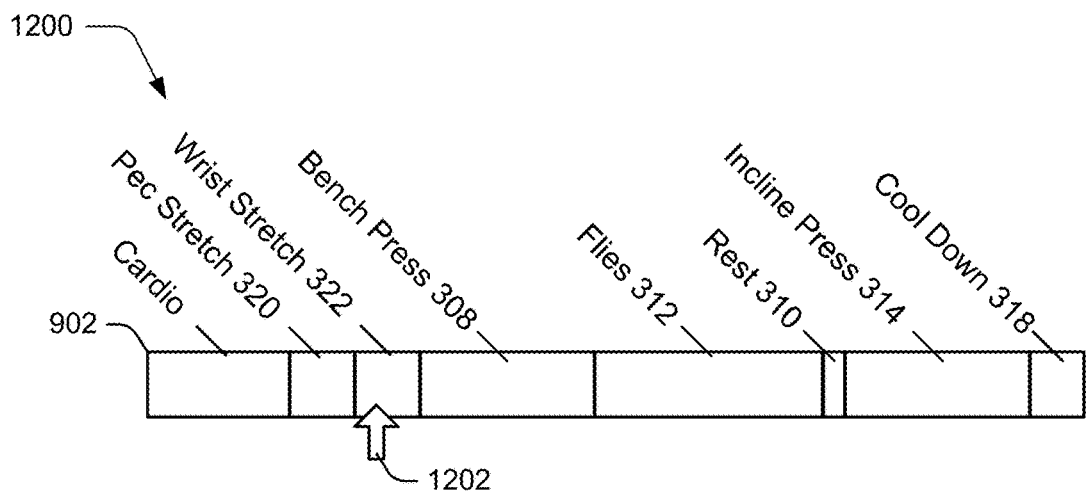
FIG. 12 illustrates an example implementation scenario in accordance with one or more embodiments.
Figure 12:
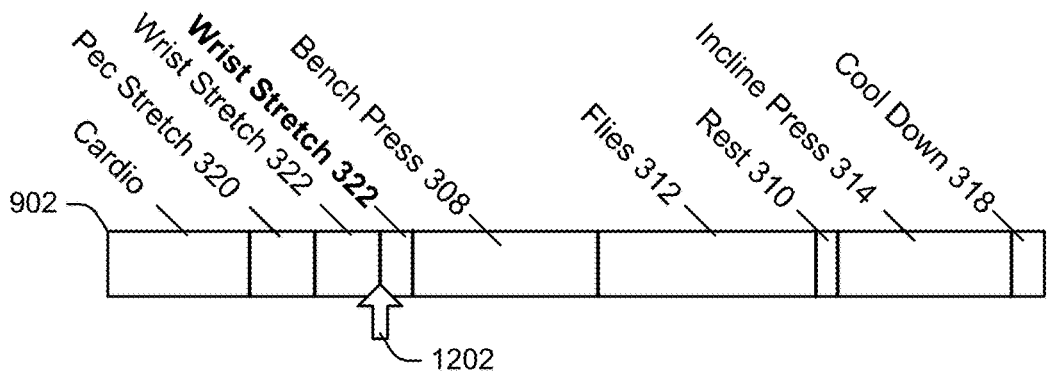

FIG. 12 illustrates another example implementation scenario in which an exercise routine is dynamically modified, generally at 1100. Starting with the upper portion of the scenario 1200, a user exercises along with the playback of the exercise routine 902, discussed above. The playback progress of the exercise routine 902 is indicated by the progress indicator 1202.

Continuing to the middle portion of the scenario 1200, user-associated feedback is received that indicates that the user wishes the repeat the first 3 minutes of the wrist stretch section 322. For example, perhaps the user is sore from a previous workout and wishes to perform further stretching.

Continuing to the lower portion of the scenario 1200, and in response to the user-associated feedback, the first three minutes of the wrist stretch section 322 is duplicated within the exercise routine 902. For example, the first three minutes of the wrist stretch section 322 can be repeated during playback of the exercise routine 902. In implementations, to stay within a 60 minute parameter for the exercise routine 902, portions of subsequent exercise segments can be removed to enable the first three minutes of the wrist stretch section 322 to be duplicated. For example, portions of the incline press segment 314 and/or the cool down segment 318 can be removed.

Implementations may also repeat particular portions of exercise content based on detected performance attributes.

For example, techniques can detect that a user's form while performing a particular exercise is improving during playback of a segment of exercise content. Thus, instead of transitioning to a different exercise, some or all of the segment that includes the particular exercise can be repeated to enable the user to continue to work on their form. Thus, techniques can customize exercise content during playback to repeat particular portions based on explicit input from a user, and/or based on performance-related attributes that are detected from a user.

Figure 13:
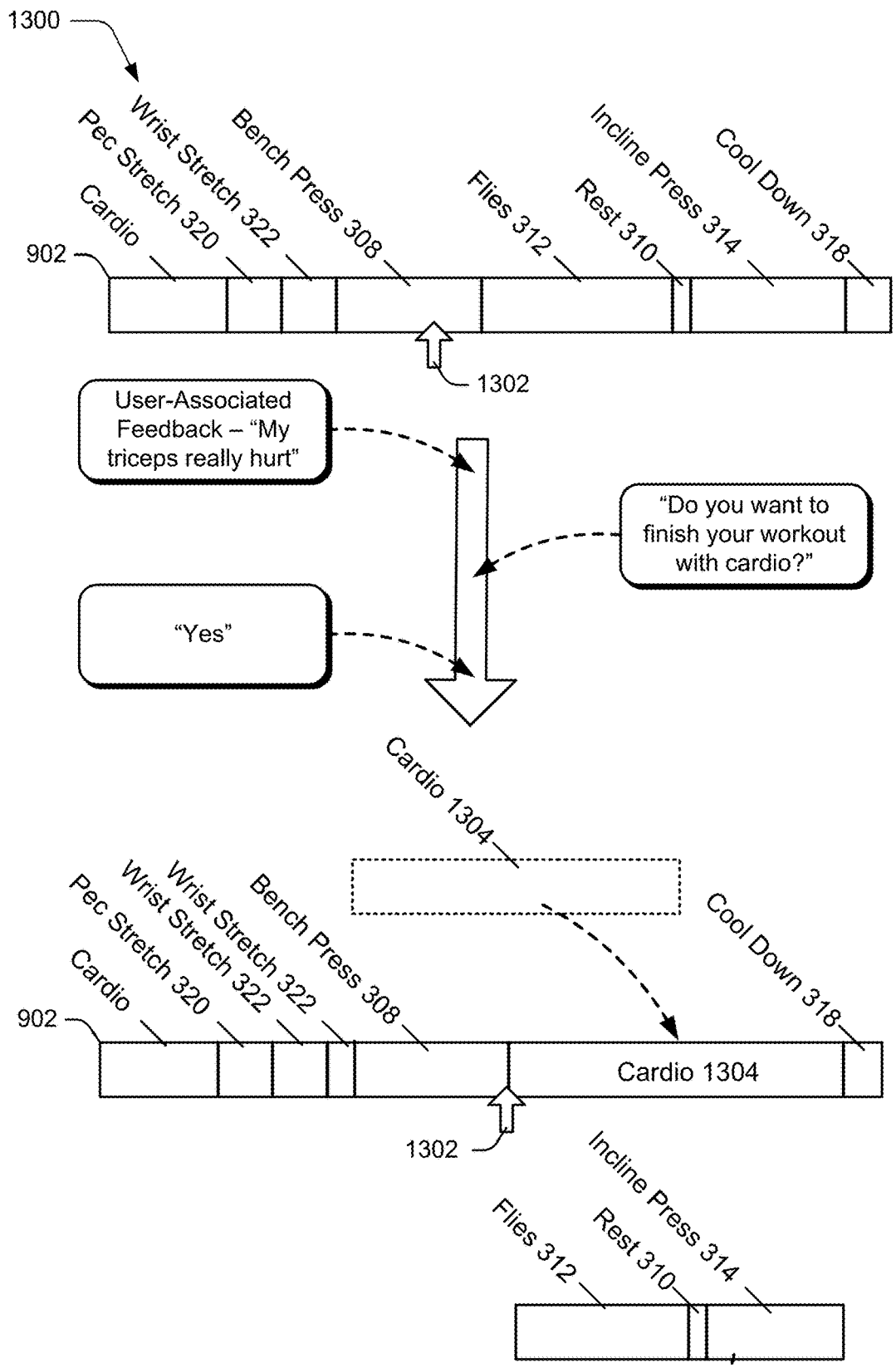
FIG. 13 illustrates an example implementation scenario in accordance with one or more embodiments.

FIG. 13 illustrates another example implementation scenario in which an exercise routine is dynamically modified, generally at 1300. Starting with the upper portion of the scenario 1300, a user exercises along with the playback of the exercise routine 902, discussed above. The playback progress of the exercise routine 902 is indicated by the progress indicator 1302.

Continuing to the middle portion of the scenario 1300, user-associated feedback is received that indicates that the user is feeling pain in their triceps muscle. For example, the user can say "my triceps really hurt." In response, the user is asked "Do you want to finish your workout with cardio?" The exercise manager module 106, for instance, can cause audible and/or text output requesting whether the user wants to finish their workout with cardio. The user answers "Yes."

Proceeding to the lower portion of the scenario 1300, and in response to the user answering "Yes," the remaining chest exercises (e.g., the flies 312 and the incline press 314 segments) of the exercise routine 902 are replaced with a cardio segment 1304 that includes cardio exercises. Thus, the user can finish the remainder of their exercise period using cardio exercises, instead of the chest exercises originally retrieved for playback.

Note that in this example, the cool down segment 318 is retained. Thus, when exercise content is dynamically modified, portions of exercise content can be replaced and other portions can be retained based on the parameters of the dynamic modification. For instance, in this example the cool down segment 318 would most likely not put stress on the user's triceps muscles, and thus is retained to allow the user to cool down after the cardio segment 1304.

Augmentation of Exercise Content

Techniques can augment exercise content by inserting, deleting, and/or modifying visual images, audio content, and so on.

Figure 14:
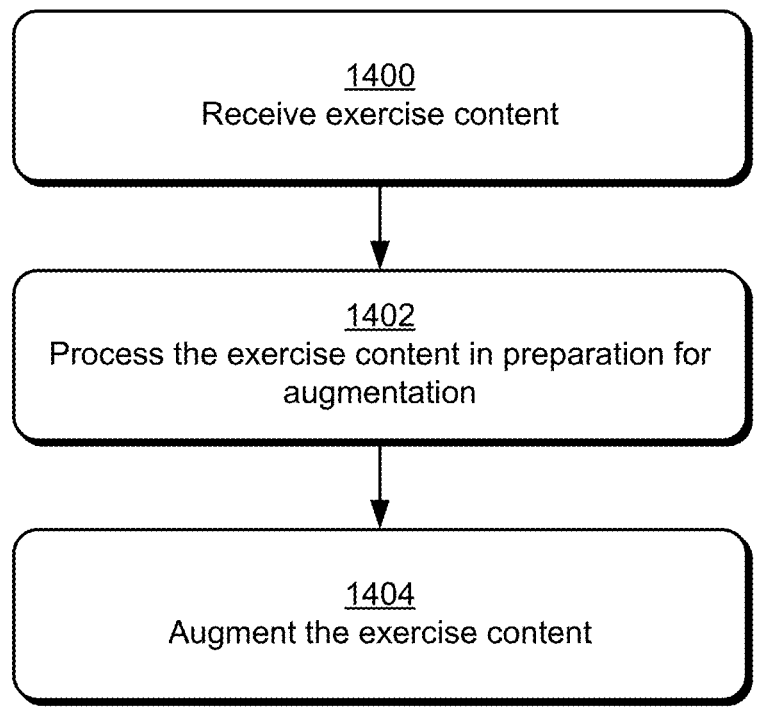
FIG. 14 is a flow diagram that describes steps in a method in accordance with one or more embodiments.

FIG. 14 is a flow diagram that describes steps in a method in accordance with one or more embodiments. Step 1400 receives exercise content. For example, the exercise content can be pre-recorded exercise content, such as a content stream, a content segment, and/or a content clip. In implementations, the exercise content can be "off the shelf" exercise content, such as exercise content that is retrieved from a pre-recorded DVD or other data storage medium, downloaded from a network resource, and so on.

Step 1402 processes the exercise content in preparation for augmentation. For example, 2D and/or 3D image processing techniques can be utilized to extract information about visual depth in scenes of the exercise content, to identify actors, props, and/or empty spaces within the exercise content, and so on. Such techniques can also be utilized to remove actors and/or props from various scenes of the exercise content, such as actors and/or props that were captured when the exercise content was originally recorded. In implementations, the exercise content can be pre-processed before it is obtained (e.g., purchased) by a user. Alternatively or additionally, the exercise content can be processed at runtime. For example, the exercise content can be processed after a user initiates playback of the exercise content, but before the playback actually begins.

Step 1404 augments the exercise content. For example, a representation of a user (e.g., captured by the NUI device 120) can be inserted into scenes (e.g., frames) of the exercise content using digital image processing techniques. A representation of a user, for instance, can be inserted in an empty space of a scene. The empty space can be a space where an actor or prop was removed during processing, or a space identified as being empty during processing. The representation of the user can include captured video images of the user that are enhanced using digital image processing techniques, e.g., CGI. Further, virtual props, such as hurdles, cones, and so on, can be inserted such that the user can interact with the virtual props as part of an exercise experience. Performance feedback can be presented by visually emphasizing portions of the user representation.

In implementations, lighting information about exercise content can also be extracted, e.g., via light probes. In implementations, a light probe is an omnidirectional image that records incident illumination conditions at particular points in an environment. The lighting information can be used to light and/or shade user images and virtual 3D props that are inserted into exercise content so that they can better match the pre-recorded environment included in the exercise content.

Figure 15:
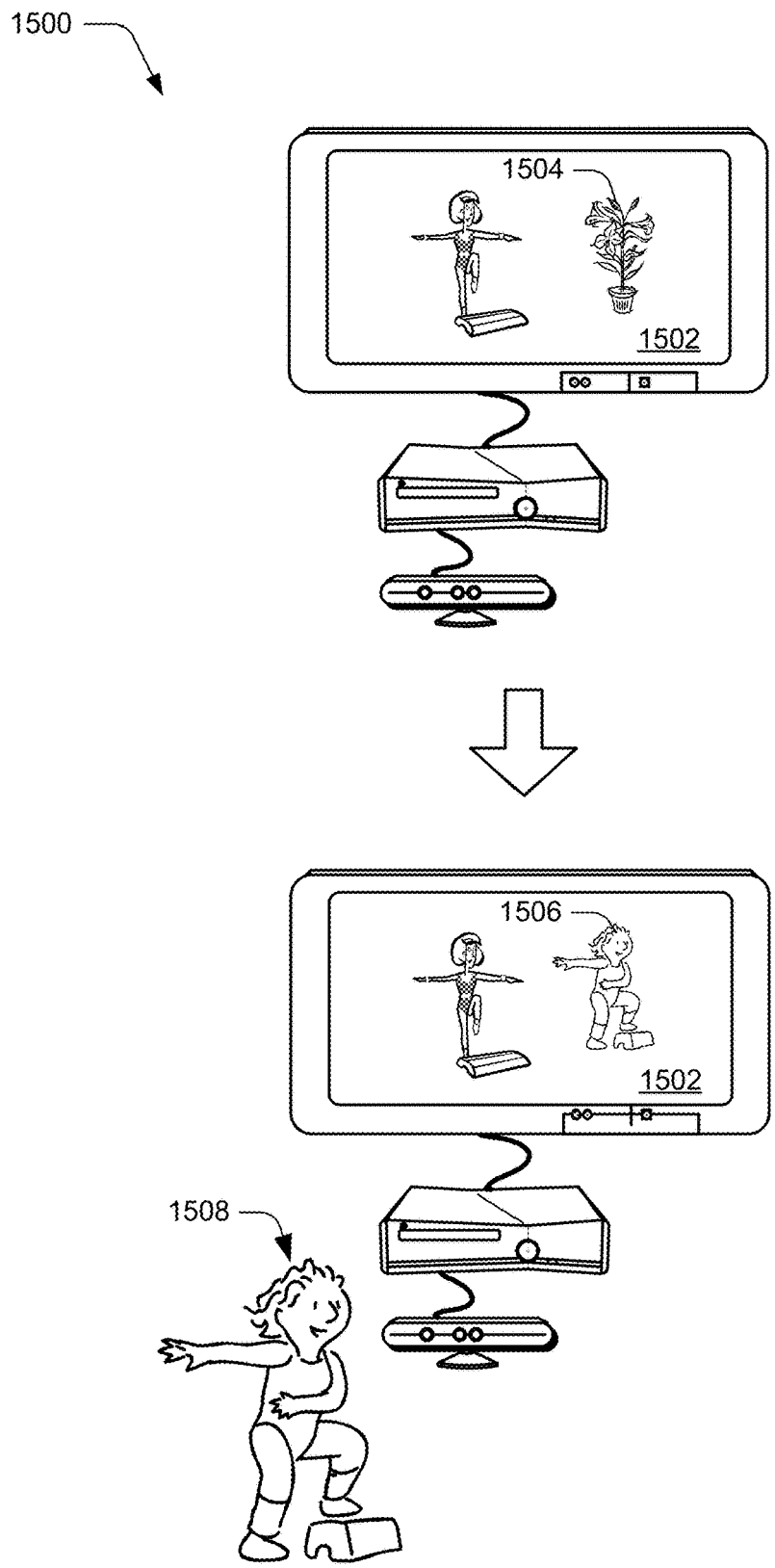
FIG. 15 illustrates an example implementation scenario in accordance with one or more embodiments.

FIG. 15 illustrates an example implementation scenario in which exercise content is augmented, generally at 1500. Beginning with the upper portion of the scenario 1500, exercise content 1502 is initiated that includes a prop 1504 that was captured when the exercise content 1502 was initially recorded.

Continuing to the lower portion of the scenario 1500, the exercise content 1502 is processed to remove the prop 1504 from the exercise content 1502. The exercise content 1502 is then augmented to insert an image 1506 of a user 1508 into the display of the exercise content 1502. For example, the image 1506 can be inserted in a visual region of the exercise content 1502 that was previously occupied by the prop 1504. Further, the image 1506 can be a "real time" image such that the image 1506 moves along with movement of the user 1508, such as to track movements of the user 1508 as part of an exercise routine. With reference to the environment 100 discussed above, the image 1506 can be used instead of the user region 130, or in addition to the user region 130.

Example System and Device

Figure 16:
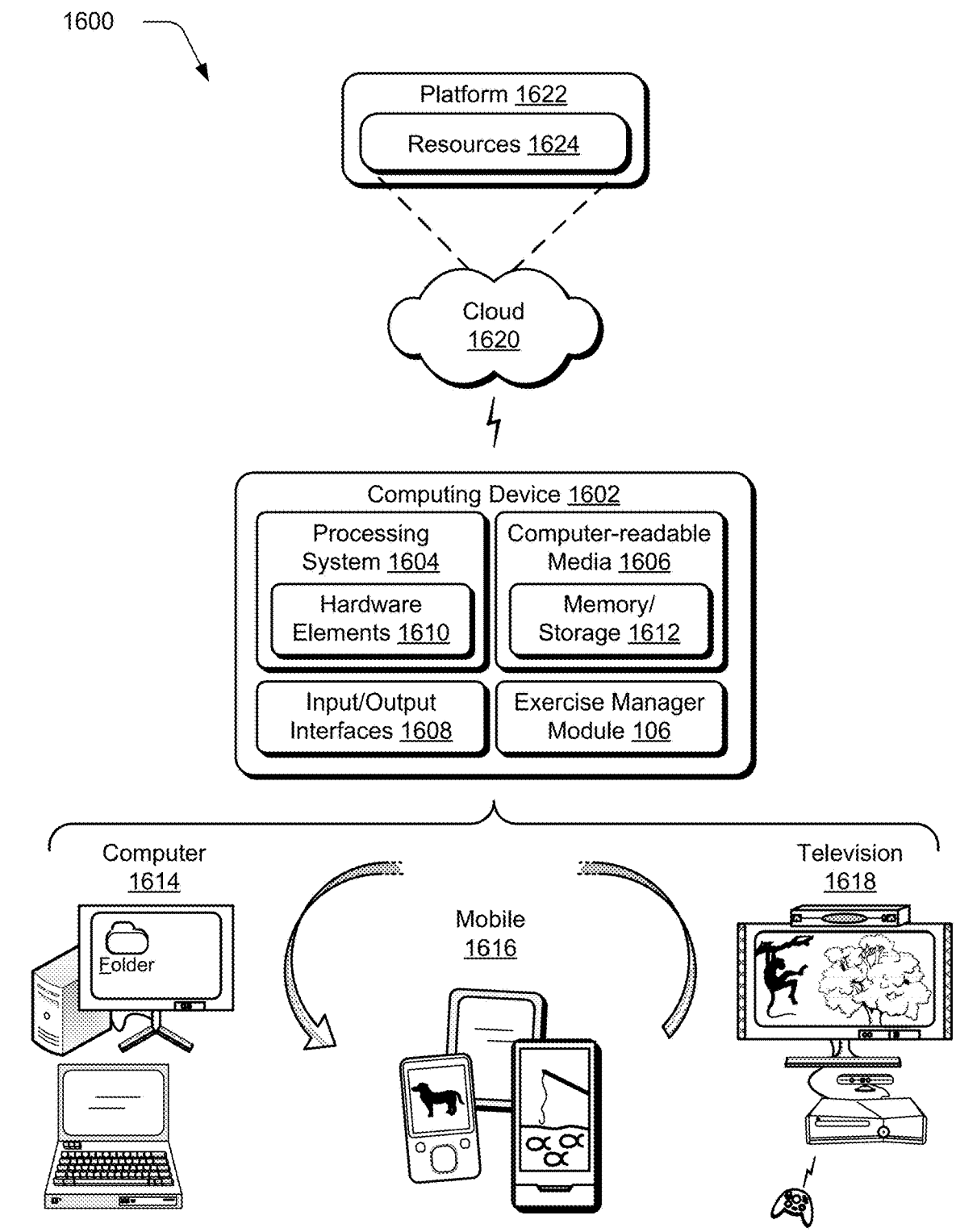
FIG. 16 illustrates an example system and computing device as described with reference to FIG. 1, which are configured to implement embodiments of techniques described herein.

FIG. 16 illustrates an example system generally at 1600 that includes an example computing device 1602 that is representative of one or more computing systems and/or devices that may implement various techniques described herein. The computing device 1602 may be, for example, a server of a service provider, a device associated with the client (e.g., a client device), an on-chip system, and/or any other suitable computing device or computing system.

The example computing device 1602 as illustrated includes a processing system 1604, one or more computer-readable media 1606, and one or more I/O Interfaces 1608 that are communicatively coupled, one to another. Although not shown, the computing device 1602 may further include a system bus or other data and command transfer system that couples the various components, one to another. A system bus can include any one or combination of different bus structures, such as a memory bus or memory controller, a peripheral bus, a universal serial bus, and/or a processor or local bus that utilizes any of a variety of bus architectures. A variety of other examples are also contemplated, such as control and data lines.

The processing system 1604 is representative of functionality to perform one or more operations using hardware. Accordingly, the processing system 1604 is illustrated as including hardware element 1610 that may be configured as processors, functional blocks, and so forth. This may include implementation in hardware as an application specific integrated circuit or other logic device formed using one or more semiconductors. The hardware elements 1610 are not limited by the materials from which they are formed or the processing mechanisms employed therein. For example, processors may be comprised of semiconductor(s) and/or transistors (e.g., electronic integrated circuits (ICs)). In such a context, processor-executable instructions may be electronically-executable instructions.

The computer-readable media 1606 is illustrated as including memory/storage 1612. The memory/storage 1612 represents memory/storage capacity associated with one or more computer-readable media. The memory/storage 1612 may include volatile media (such as random access memory (RAM)) and/or nonvolatile media (such as read only memory (ROM), Flash memory, optical disks, magnetic disks, and so forth). The memory/storage 1612 may include fixed media (e.g., RAM, ROM, a fixed hard drive, and so on) as well as removable media (e.g., Flash memory, a removable hard drive, an optical disc, and so forth). The computer-readable media 1606 may be configured in a variety of other ways as further described below.

Input/output interface(s) 1608 are representative of functionality to allow a user to enter commands and information to computing device 1602, and also allow information to be presented to the user and/or other components or devices using various input/output devices. Examples of input devices include a keyboard, a cursor control device (e.g., a mouse), a microphone, a scanner, touch functionality (e.g., capacitive or other sensors that are configured to detect physical touch), a camera (e.g., which may employ visible or non-visible wavelengths such as infrared frequencies to detect movement that does not involve touch as gestures), and so forth. Examples of output devices include a display device (e.g., a monitor or projector), speakers, a printer, a network card, tactile-response device, and so forth. Thus, the computing device 1602 may be configured in a variety of ways as further described below to support user interaction.

Various techniques may be described herein in the general context of software, hardware elements, or program modules. Generally, such modules include routines, programs, objects, elements, components, data structures, and so forth that perform particular tasks or implement particular abstract data types. The terms "module," "functionality," and "component" as used herein generally represent software, firmware, hardware, or a combination thereof. The features of the techniques described herein are platform-independent, meaning that the techniques may be implemented on a variety of commercial computing platforms having a variety of processors.

An implementation of the described modules and techniques may be stored on or transmitted across some form of computer-readable media. The computer-readable media may include a variety of media that may be accessed by the computing device 1602. By way of example, and not limitation, computer-readable media may include "computer-readable storage media" and "computer-readable signal media."

"Computer-readable storage media" may refer to media and/or devices that enable persistent and/or non-transitory storage of information in contrast to mere signal transmission, carrier waves, or signals per se. Thus, computer-readable storage media does not include transitory signal bearing media. The computer-readable storage media includes hardware such as volatile and non-volatile, removable and non-removable media and/or storage devices implemented in a method or technology suitable for storage of information such as computer readable instructions, data structures, program modules, logic elements/circuits, or other data. Examples of computer-readable storage media may include, but are not limited to, RAM, ROM, EEPROM, flash memory or other memory technology, CD-ROM, digital versatile disks (DVD) or other optical storage, hard disks, magnetic cassettes, magnetic tape, magnetic disk storage or other magnetic storage devices, or other storage device, tangible media, or article of manufacture suitable to store the desired information and which may be accessed by a computer.

"Computer-readable signal media" may refer to a signal-bearing medium that is configured to transmit instructions to the hardware of the computing device 1602, such as via a network. Signal media typically may embody computer readable instructions, data structures, program modules, or other data in a modulated data signal, such as carrier waves, data signals, or other transport mechanism. Signal media also include any information delivery media. The term "modulated data signal" means a signal that has one or more of its characteristics set or changed in such a manner as to encode information in the signal. By way of example, and not limitation, communication media include wired media such as a wired network or direct-wired connection, and wireless media such as acoustic, RF, infrared, and other wireless media.

As previously described, hardware elements 1610 and computer-readable media 1606 are representative of instructions, modules, programmable device logic and/or fixed device logic implemented in a hardware form that may be employed in some embodiments to implement at least some aspects of the techniques described herein. Hardware elements may include components of an integrated circuit or on-chip system, an application-specific integrated circuit (ASIC), a field-programmable gate array (FPGA), a complex programmable logic device (CPLD), and other implementations in silicon or other hardware devices. In this context, a hardware element may operate as a processing device that performs program tasks defined by instructions, modules, and/or logic embodied by the hardware element as well as a hardware device utilized to store instructions for execution, e.g., the computer-readable storage media described previously.

Combinations of the foregoing may also be employed to implement various techniques and modules described herein. Accordingly, software, hardware, or program modules and other program modules may be implemented as one or more instructions and/or logic embodied on some form of computer-readable storage media and/or by one or more hardware elements 1610. The computing device 1602 may be configured to implement particular instructions and/or functions corresponding to the software and/or hardware modules. Accordingly, implementation of modules as an module that is executable by the computing device 1602 as software may be achieved at least partially in hardware, e.g., through use of computer-readable storage media and/or hardware elements 1610 of the processing system. The instructions and/or functions may be executable/operable by one or more articles of manufacture (for example, one or more computing devices 1602 and/or processing systems 1604) to implement techniques, modules, and examples described herein.

As further illustrated in FIG. 15, the example system 1600 enables ubiquitous environments for a seamless user experience when running applications on a personal computer (PC), a television device, and/or a mobile device. Services and applications run substantially similar in all three environments for a common user experience when transitioning from one device to the next while utilizing an application, playing a video game, watching a video, and so on.

In the example system 1600, multiple devices are interconnected through a central computing device. The central computing device may be local to the multiple devices or may be located remotely from the multiple devices. In one embodiment, the central computing device may be a cloud of one or more server computers that are connected to the multiple devices through a network, the Internet, or other data communication link.

In one embodiment, this interconnection architecture enables functionality to be delivered across multiple devices to provide a common and seamless experience to a user of the multiple devices. Each of the multiple devices may have different physical requirements and capabilities, and the central computing device uses a platform to enable the delivery of an experience to the device that is both tailored to the device and yet common to all devices. In one embodiment, a class of target devices is created and experiences are tailored to the generic class of devices. A class of devices may be defined by physical features, types of usage, or other common characteristics of the devices.

In various implementations, the computing device 1602 may assume a variety of different configurations, such as for computer 1614, mobile 1616, and television 1618 uses. Each of these configurations includes devices that may have generally different constructs and capabilities, and thus the computing device 1602 may be configured according to one or more of the different device classes. For instance, the computing device 1602 may be implemented as the computer 1614 class of a device that includes a personal computer, desktop computer, a multi-screen computer, laptop computer, netbook, and so on.

The computing device 1602 may also be implemented as the mobile 1616 class of device that includes mobile devices, such as a mobile phone, portable music player, portable gaming device, a tablet computer, a multi-screen computer, and so on. The computing device 1602 may also be implemented as the television 1618 class of device that includes devices having or connected to generally larger screens in casual viewing environments. These devices include televisions, set-top boxes, gaming consoles, and so on.

The techniques described herein may be supported by these various configurations of the computing device 1602 and are not limited to the specific examples of the techniques described herein. This is illustrated through inclusion of the exercise manager module 106 on the computing device 1602. The functionality of the exercise manager module 106 and other modules described with reference to FIG. 1 may also be implemented all or in part through use of a distributed system, such as over a "cloud" 1620 via a platform 1622 as described below.

The cloud 1620 includes and/or is representative of a platform 1622 for resources 1624. The platform 1622 abstracts underlying functionality of hardware (e.g., servers) and software resources of the cloud 1620. The resources 1624 may include applications and/or data that can be utilized while computer processing is executed on servers that are remote from the computing device 1602. Resources 1624 can also include services provided over the Internet and/or through a subscriber network, such as a cellular or Wi-Fi network.

The platform 1622 may abstract resources and functions to connect the computing device 1602 with other computing devices. The platform 1622 may also serve to abstract scaling of resources to provide a corresponding level of scale to encountered demand for the resources 1624 that are implemented via the platform 1622. Accordingly, in an interconnected device embodiment, implementation of functionality described herein may be distributed throughout the system 1600. For example, the functionality may be implemented in part on the computing device 1602 as well as via the platform 1622 that abstracts the functionality of the cloud 1620.

Discussed herein are a number of methods that may be implemented to perform techniques discussed herein. Aspects of the methods may be implemented in hardware, firmware, or software, or a combination thereof. The methods are shown as a set of blocks that specify operations performed by one or more devices and are not necessarily limited to the orders shown for performing the operations by the respective blocks. Further, an operation shown with respect to a particular method may be combined and/or interchanged with an operation of a different method in accordance with one or more implementations. Aspects of the methods can be implemented via interaction between various entities discussed above with reference to the environment 100.

CONCLUSION

Techniques for dynamic exercise content are described. Although embodiments are described in language specific to structural features and/or methodological acts, it is to be understood that the embodiments defined in the appended claims are not necessarily limited to the specific features or acts described. Rather, the specific features and acts are disclosed as example forms of implementing the claimed embodiments.

What is claimed is:

1. A system comprising:
light sensors;
a Natural User Interface (NUI) configured to detect points on a human body via the light sensors;
one or more processors; and
one or more computer-readable storage media storing instructions that are executable by the one or more processors to perform operations including:
receiving parameters that are specific to a user;
acquiring historic data specific to the user;
selecting a set of segments from different individually selectable segments of pre-recorded content based on the received parameters and the acquired historic data specific to the user;
generating, based at least on the received parameters and the acquired historic data specific to the user, a custom content stream that includes the selected set of segments;
causing at least a portion of the custom content stream to be output to a display;
during a playback of the custom content stream, detecting one or more of a gesture, a pose, or a body movement of the user received via the light sensors;

upon detecting the one or more of the gesture, the pose, or the body movement of the user received via the light sensors, identifying particular points of the body; and using the particular points of the body to compare parameters of the one or more of the gesture, the pose, or the body movement to known parameters for the one or more of the gesture, the pose, or the body movement to determine whether the one or more of the gesture, the pose, or the body movement is being performed properly based on instructions of the custom content stream output to the display;

modifying the custom content stream based on whether the one or more of the gesture, the pose, or the body movement is determined to be performed properly, wherein the modification of the custom content stream comprises one or more of the following: applying new segments of content to the custom content stream, repeating content that has already been played in the custom content stream, changing a pace at which the custom content stream is provided, and rearranging content that has already been retrieved in the custom content stream;

receiving a visual representation of the user captured by the NUI such that movements of the user are reflected in similar movements of the visual representation of the user; and causing an output of the visual representation with the modified custom content stream to the display.

2. A system as described in claim 1, wherein the parameters comprise at least one of physical attributes of the user or exercise-related abilities of the user.

3. A system as described in claim 1, wherein the light sensors are configured to sense vertical movement, horizontal movement, and forward and backward movement relative to the NUI.

4. A system as described in claim 3, wherein the light sensors capture information about image composition, movement, and/or position.

5. A system as described in claim 1, wherein the individually selectable segments are selected from at least one of selectable segments of one or more content streams, or one or more content clips.

6. A system as described in claim 1, wherein the operations further include:
receiving user-associated feedback during playback of the at least a portion of the custom content stream; and
modifying the custom content stream based on the user-associated feedback.

7. A system as described in claim 1, wherein the operations further include:
receiving user-associated feedback during playback of the at least a portion of the custom content stream; and
providing performance feedback based on the user-associated feedback.

8. A system as described in claim 7, wherein the performance feedback comprises one or more of a visual or an audible indication of user performance of an activity.

9. A system as described in claim 1, wherein the acquired historic data comprises one or more of the following: a user profile, user preferences, and user content history.

10. A computer-implemented method comprising:
receiving input detected by a light sensor of a Natural User Interface (NUI) device during playback of content to detect points on a body of a user;
receiving parameters that are specific to the user;
acquiring historic data specific to the user;
generating a representation of the user based on the received input detected by the light sensor;
displaying the representation of the user on a display in real time such that movements of the user are reflected in similar movements of the representation of the user;
executing logic by a computing device to interpret the input detected by the light sensor as the user performs a portion of an exercise routine relating to a playback of an exercise routine content on the display;
responsive to interpreting the input detected by the light sensor as the user performing the portion of the exercise routine:
executing logic by the computing device to dynamically modify the playback of the exercise routine content comprising one or more segments based on a comparison of the user performance of the portion of the exercise routine to known parameters for the exercise routine content during playback of the exercise routine content and the acquired historic data specific to the user; and
causing dynamically modified playback of the exercise routine content to be displayed on the display with the representation of the user in real time, wherein the dynamically modified playback comprises one or more of the following: applying new segments of content to the exercise routine content, repeating content that has already been played in the exercise routine content, changing a pace at which the exercise routine content is played back, and rearranging content that has already been retrieved in the exercise routine content.

11. A computer-implemented method as described in claim 10, wherein the dynamically modified playback comprises an indication of user performance of one or more activities as detected by the NUI device.

12. A computer-implemented method as described in claim 10, wherein the input comprises at least one of voice or gesture feedback detected by the NUI device from the user.

13. A computer-implemented method as described in claim 10, wherein said modifying occurs dynamically during playback of one or more portions of the exercise routine content.

14. A computer-implemented method as described in claim 10, wherein said modifying comprises selecting one or more subsequent portions of the exercise routine content based on the comparison of the user performance of the portion of the exercise routine to the known parameters for the exercise routine content.

15. A computer-implemented method as described in claim 10, wherein said modifying comprises replacing one or more portions of the exercise routine content with one or more different portions of content.

16. A computer-implemented method as described in claim 10, further comprising updating user profile data based on the comparison of the user performance of the portion of the exercise routine to the known parameters for the exercise routine content, wherein the user profile data is accessible to determine one or more subsequent selections of content.

17. A computer-implemented method, comprising:
displaying an exercise routine content stream on a display;
receiving, by a computing device, parameters that are detected by a light sensor of a Natural User Interface (NUI) device;

during a playback of the exercise routine content stream:
   acquiring historic data specific to a user;
   identifying particular points of a body of the user detected by the light sensor;
   based on the identified particular points of the body of the user, identifying one or more of a gesture, a pose, or a body movement of the user detected by the light sensor;
   executing logic by the computing device to dynamically select a set of segments from different individually selectable segments of pre-recorded content based at least on the received parameters and the acquired historic data specific to the user and the one or more of the gesture, the pose, or the body movement, at least some segments of the set of segments being selected from different content streams that include different respective segments of the individually selectable segments;
   updating the exercise routine content stream to include the selected set of segments;
   receiving a visual representation of the user captured by the NUI device such that movements of the user are reflected in similar movements of the visual representation of the user;
   inserting the visual representation into the pre-recorded content; and
   causing an output of the visual representation with the updated exercise routine content stream to the display.

18. A computer-implemented method as described in claim 17, wherein the parameters are captured by a second light sensor of the NUI device.

19. A computer-implemented method as described in claim 17, wherein the parameters comprise one or more of gender, age, height, and weight of the user detected by the NUI device.

20. A computer-implemented method as described in claim 17,
   wherein the individually selectable segments are selected from at least one of selectable segments of one or more content streams or one or more content clips.

* * * * *